US012759994B2

(12) United States Patent
An et al.

(10) Patent No.: US 12,759,994 B2
(45) Date of Patent: Oct. 13, 2026

(54) ISOLATION METHOD FOR LACTIDE RACEMATE

(71) Applicant: LG CHEM, LTD., Seoul (KR)

(72) Inventors: Yujin An, Daejeon (KR); Hyunchul Jung, Daejeon (KR); Wan Kyu Oh, Daejeon (KR)

(73) Assignee: LG CHEM, LTD., Seoul (KR)

( * ) Notice: Subject to any disclaimer, the term of this patent is extended or adjusted under 35 U.S.C. 154(b) by 643 days.

(21) Appl. No.: 18/272,034

(22) PCT Filed: Jun. 8, 2022

(86) PCT No.: PCT/KR2022/008085
§ 371 (c)(1),
(2) Date: Sep. 18, 2023

(87) PCT Pub. No.: WO2022/260430
PCT Pub. Date: Dec. 15, 2022

(65) Prior Publication Data

US 2024/0343702 A1 Oct. 17, 2024

(30) Foreign Application Priority Data

Jun. 10, 2021 (KR) ........................ 10-2021-0075600
Jun. 7, 2022 (KR) ........................ 10-2022-0069132

(51) Int. Cl.
*C07D 319/12* (2006.01)
*C07B 63/00* (2006.01)

(52) U.S. Cl.
CPC ............ *C07D 319/12* (2013.01); *C07B 63/00* (2013.01)

(58) Field of Classification Search
CPC .............................. C07D 319/12; C07B 63/00
See application file for complete search history.

(56) References Cited

U.S. PATENT DOCUMENTS

| | | | |
|---|---|---|---|
| 5,502,215 | A | 3/1996 | Yamaguchi et al. |
| 6,022,409 | A | 2/2000 | Coquerel et al. |
| 2008/0207944 | A1 | 8/2008 | Morgensternet et al. |
| 2010/0261916 | A1 | 10/2010 | Wu et al. |
| 2012/0095240 | A1 | 4/2012 | Benson et al. |
| 2012/0197040 | A1 | 8/2012 | Lorenz et al. |
| 2014/0141475 | A1 | 5/2014 | Marshall et al. |
| 2014/0147898 | A1 | 5/2014 | Marshall et al. |
| 2014/0342413 | A1 | 11/2014 | Marshall et al. |

FOREIGN PATENT DOCUMENTS

| | | | |
|---|---|---|---|
| CN | 102285664 | B | 6/2013 |
| CN | 103687955 | A | 3/2014 |
| CN | 102875522 | B | 6/2014 |
| CN | 106995429 | A | 8/2017 |
| CN | 112047920 | A | 12/2020 |
| CN | 112142968 | A | 12/2020 |
| DE | 4407036 | A1 | 9/1995 |
| DE | 102005039501 | A1 | 2/2007 |
| EP | 2292306 | A1 | 3/2011 |
| JP | 07-165753 | A | 6/1995 |
| JP | 2012-520322 | A | 9/2012 |
| JP | 2014-521601 | A | 8/2014 |
| JP | 2014-522651 | A | 9/2014 |
| JP | 2014-522652 | A | 9/2014 |
| KR | 10-0592794 | B1 | 6/2006 |
| KR | 10-2008-0018650 | A | 2/2008 |
| KR | 10-2010-0095547 | A | 8/2010 |
| KR | 10-2014-0053129 | A | 5/2014 |
| KR | 10-2015-0060116 | A | 6/2015 |
| KR | 10-1809663 | B1 | 12/2017 |
| WO | 2007-023129 | A2 | 3/2007 |

OTHER PUBLICATIONS

Tao et al. "Research advances in purification process of lactide," Chemical Industry and Engineering Progress, Dec. 31, 2010, pp. 215-221 (English abstract only).

Lorenz et al., "Application of Preferential Crystallization to Resolve Racemic Compounds in a Hybrid Process", Chiralty 18: 828-840 (2006).

*Primary Examiner* — Rebecca L Anderson
(74) *Attorney, Agent, or Firm* — Bryan Cave Leighton Paisner LLP

(57) ABSTRACT

Provided is an isolation method capable of isolating lactide racemate with high yield and with high efficiency, without concern for side reactions, even when the amount of L-lactide is low.

11 Claims, 4 Drawing Sheets

ISOLATION METHOD FOR LACTIDE RACEMATE

CROSS-REFERENCE TO RELATED APPLICATION(S)

This application is a National Stage Application of International Application No. PCT/KR2022/008085 filed on Jun. 8, 2022, which claims priority to and the benefit of Korean Patent Application No. 10-2021-0075600 filed on Jun. 10, 2021 and Korean Patent Application No. 10-2022-0069132 filed on Jun. 7, 2022 with the Korean Intellectual Property Office, the disclosures of which are herein incorporated by reference in their entirety.

TECHNICAL FIELD

This invention relates to a method for isolating lactide racemate with high yield and high efficiency without side reactions.

BACKGROUND

Polylactic acid not only has biodegradability, but also has excellent mechanical properties such as tensile strength and elasticity, and is being widely used in various fields. Although polylactic acid is homopolymer, it can have various structures due to stereoregularity. Polylactic acid is generally prepared through ring opening polymerization of lactide (LT), but since optical isomers of lactide exist, the properties of polylactic acid can vary according to the arrangement of such optical isomers in the repeat unit.

Meanwhile, lactide is lactic acid dimer, which is cyclic di-ester of lactic acid (2-hydroxypropionic acid, LA), and it was prepared by a reactive distillation method wherein lactic acid is subjected to a dehydration reaction to obtain lactic acid oligomer having relatively low molecular weight as an intermediate, and it is heated to 180° C. or more in the presence of a catalyst and decompressed to depolymerize-cyclize, thus forming lactide, and then, it is discharged as steam outside a reactor.

Since lactic acid used for the preparation of lactide is a chiral molecule having D-(or (R)-) and L-(or(S)-) enantiomers, lactide produced from the lactic acid exists as three optical isomers having two stereocenters, specifically, L-lactide (L-LT) or (S,S)-lactide formed from two molecules of L-lactic acid, D-lactide (D-LT) or (R,R)-lactide formed from two molecules of D-lactic acid, and meso-lactide (meso-LT) or (R,S)-lactide formed from each one molecule of L-lactic acid and D-lactic acid. Besides the optical isomer mixture, in case lactide is prepared by the reactive distillation method, unreacted lactic acid and lactic acid derivatives can also exist as impurities.

Although a lactide mixture having optical purity of 90% or more, namely, containing 90% or more of L-lactide or D-lactide can be prepared using a selective synthesis method when preparing lactide, it is difficult to produce at high purity of 99% or more. And, since meso-lactide included in the products is rapidly hydrolyzed compared to L-lactide and D-lactide, if the content of meso-lactide in the products is high, hydrolysis is generally promoted. And, lactic acid or lactic acid oligomer increases acidity and inhibits formation of high quality polylactide. Thus, there was a demand for a purification method capable of removing meso-lactide, lactic acid and lactic acid derivatives while containing L-lactide or D-lactide at high purity, according to the purpose of use.

Recently, methods of utilizing meso-lactide produced during the preparation of lactide from lactic acid are being diversely researched and developed.

For example, meso-lactide is converted into L-lactide and D-lactide through racemization. However, lactide converted through racemization is a racemate wherein the rate of L-lactide and D-lactide is 1:1, which are difficult to isolate because of identical physical and chemical properties.

As a method for isolating the racemate, melt-crystallization, simultaneous crystallization using seed introduction, use of chiral solvent, and the like have been suggested. However, the melt-crystallization can be conducted only when the L-lactide amount is 80% or more. And, as a method of using seed introduction and an ethanol solvent, L-lactide is introduced as a seed, and then, L-lactide is isolated using an ethanol solvent, but this method is effective only when the L-lactide amount is 60% or more.

Thus, there is demand for the development of a method capable of isolating lactide racemate with high yield and high efficiency without concern about side reactions, even when the amount of L-lactide is low.

DETAILED DESCRIPTION

Technical Problem

It is an object of the invention to provide a method capable of isolating lactide racemate with high yield and high efficiency, without concern about side reactions, even when the amount of L-lactide is low.

Technical Solution

In order to achieve the object, provided is a method for isolating lactide racemate, comprising:

introducing L-lactide into lactide racemate and mixing them to prepare a mixture (step 1); and introducing an extraction solvent into the mixture, to selectively extract L-lactide from the lactide racemate (step 2), wherein the extraction solvent comprises an amine-based compound or an amide-based compound.

The present invention relates to a method for separating lactide racemates.

Hereinafter, the invention will be explained in detail according to each step.

(Step 1)

In the isolation method of lactide racemate of the invention, step 1 is a step of introducing L-lactide into lactide racemate and mixing them to prepare a mixture.

The lactide racemate is a mixture of optical isomers in which L-lactide and D-lactide are mixed in an equal amount, and specifically, it comprises L-lactide and D-lactide at a weight ratio of 1:1.

The lactide racemate can be prepared through racemization of meso-lactide produced from side reactions during the preparation of lactide using lactic acid. Thus, the invention can further comprise a step of conducting racemization of meso-lactide to prepare lactide racemate comprising L-lactide and D-lactide, before step 1 of introducing L-lactide into lactide racemate and mixing them.

The L-lactide introduced in lactide racemate serves as a crystal seed, during the extraction reaction for isolating lactide racemate.

The L-lactide can be introduced in an amount of 10 to 70 parts by weight, based on 100 parts by weight of the lactide racemate. More specifically, the L-lactide can be introduced in such an amount that the content of L-lactide can become greater than 50 wt % and 80 wt % or less, more specifically, greater than 50 wt %, or 52 wt % or more, or 55 wt % or more, and 80 wt % or less, or 75 wt % or less, or 70 wt % or less, or 65 wt % or less, or 60 wt % or less, or less than 60 wt %, based on the total weight of the mixture obtained after introducing L-lactide in lactide racemate.

As the introduction amount of L-lactide and the content of L-lactide in the mixture are higher, L-lactide can be obtained with higher purity. Thus, in order to improve extraction selectivity and improve the decrease of impurity content, the L-lactide can be introduced in such an amount that the content of L-lactide can become 65 wt % or more, or 70 wt % or more, and 80 wt % or less, or 75 wt % or less, based on the total weight of the mixture obtained after introducing L-lactide in lactide racemate. However, in the present disclosure, since an optimal extraction solvent is used in the subsequent extraction process, even if the content of L-lactide in the mixture is as low as 60 wt % or less, or less than 60 wt %, it is possible to isolate L-lactide. Thus, the L-lactide can be introduced in such an amount that the content of L-lactide can become greater than 50 wt %, or 52 wt % or more, or 55 wt % or more, and 60 wt % or less, or less than 60 wt %, or 58 wt % or less, based on the total weight of the mixture.

(Step 2)

In the isolation method of lactide racemate of the invention, step 2 is a step of introducing an extraction solvent into the mixture prepared in step 1, to selectively extract L-lactide from the lactide racemate, As the extraction solvent, an amine-based compound, or an amide-based compound is used. These extraction solvents are non-chiral compounds without chiral properties, have polarities, and can exhibit excellent extraction solvent properties due to shift of eutectic point of three-component system phase of L-lactide, D-lactide, and an extraction solvent. Thus, these extraction solvents exhibit excellent extraction efficiency compared to alcohol, and the like conventionally used during the isolation of lactide racemate, and particularly, amine-based compounds such as triethylamine (TEA), and the like can exhibit high extraction efficiency even when the content of L-lactide in the mixture is low.

And, the extraction solvent exists as liquid at room temperature (20±5° C.), and it can be a polar solvent having a melting point of 25° C. or less and a boiling point of 80° C. or more. More specifically, the extraction solvent has a melting point of 25° C. or less, or 10° C. or less, and −150° C. or more, or −120° C. or more, and a boiling point of 80° C. or more or 100° C. or more, and 300° C. or less, or 250° C. or less. When the above melting point and boiling point conditions are met, stable and excellent extraction efficiency can be exhibited while minimizing generation of side reactions.

The amine-based compound can be specifically a tertiary amine of Chemical Formula 1:

[Chemical Formula 1]

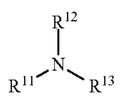

wherein in Chemical Formula 1:

$R_{11}$ to $R_{13}$ are each independently a $C_{1-20}$ linear or branched alkyl.

As specific examples of the amine-based compound, trimethylamine, triethylamine, tri-n-propylamine, tri-n-butylamine, tri-n-octylamine, tridodecylamine, trioctadecylamine, triisopropylamine, triisobutylamine, tri-t-butylamine, tris(2-ethylhexyl) amine, N,N-dilmethyloctylamine, N,N-dimethyldodecylamine, N,N-dimethyl-n-octadecylamine, or N,N-diethyldodecylamine, and the like can be mentioned, and one of them or mixtures of two or more of them can be used.

Among them, considering remarkable isolation effect, the amine-based compound can be a tertiary amine of Chemical Formula 1 wherein $R_{11}$ to $R_{13}$ are each independently a $C_{1-9}$ linear alkyl. More specifically, the amine-based compound can be triethylamine, or tri-n-octylamine.

Specifically, the amide-based compound can be a compound of Chemical Formula 2:

[Chemical Formula 2]

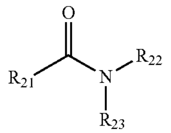

wherein in Chemical Formula 2:

each of $R_{21}$ to $R_{23}$ is hydrogen, or is independently a $C_{1-20}$ linear or branched alkyl.

The amide-based compounds of Chemical Formula 2 can exhibit more excellent isolation effect, compared to dimethylformamide, and the like that do not satisfy the $R_{21}$ to $R_{23}$ substituent requirements. More specifically, each of $R_{21}$ to $R_{23}$ is hydrogen, or independently $C_{1-8}$ linear or branched alkyl, and more specifically, each of them can be hydrogen, or methyl.

As specific examples of the amide-based compounds, formamide, or dimethylacetamide, and the like can be mentioned, and one of them or mixtures of two or more of them can be used.

The extraction solvent can be used in an amount of 1 to 10 parts by weight, based on 1 part by weight of L-lactide existing in the mixture. If the amount of the extraction solvent used is too small, extraction efficiency may not be sufficient, and if the amount of the extraction solvent used is too large, a process for removing the extraction solvent should be conducted later, thus deteriorating processability. When the extraction solvent is used within the above range, lactide racemate can be isolated with excellent extraction efficiency without additional process for removing extraction solvents. More specifically, the extraction solvent can be used in an amount of 1 part by weight or more, or 2 parts by weight or more, or 2.5 parts by weight or more, or 3 parts by weight or more, or 3.1 parts by weight or more, or 3.2 parts by weight or more, and 10 parts by weight or less, or 8 parts by weight or less, or 6.5 parts by weight or less, or 5 parts by weight or less, or 4 parts by weight or less, or 3.6 parts by weight or less, or 3.5 parts by weight or less, based on 1 part by weight of L-lactide existing in the mixture.

And, after introducing the extraction solvent in the mixture, a mixing process for uniform mixing and the resulting increase in isolation efficiency can be optionally further conducted.

Wherein, the mixing process can be conducted by a common method such as a stirrer, a mixer, and the like, and a mixing speed, time, and the like can be appropriately selected.

And, the step 2 can be conducted at a temperature of 10 to 40° C. Specifically, it can be conducted at a temperature of 10° C. or more, or 15° C. or more, and 40° C. or less, or 30° C. or less, or 25° C. or less, and more specifically, at a room temperature of 20±5° C. When the step 2 is conducted within the above temperature range, sufficiency extraction efficiency can be realized without concern about generation of side reactions.

As the result of the reaction, L-lactide is isolated from lactide racemate.

Specifically, after introducing the extraction solvent, and then, completing the optional mixing process, precipitated solids are separated and removed from the obtained reaction product through filtration, thus obtaining a filtrate.

The precipitated solids are D-lactide not dissolved in the extraction solvent and the remainder of L-lactide. An isolation process of them can be conducted by a common method, and specifically, can be isolated through filtration.

Meanwhile, in gas chromatography analysis of the filtrate, L-lactide was included in high content, specifically, in the content of 90 wt % or more, or 92 wt % or more, or 93 wt % or more, or 94 wt % or more, based on the total weight of the filtrate. And, the content of by-products formed by side reactions such as hydrolysis was less than 1 wt %, or 0.95 wt % or less, based on the total weight of the filtrate.

Advantageous Effects

As explained above, the isolation method of lactide racemate according to the invention can isolate lactide racemate with high yield and high efficiency, without concern about side reactions, even when the amount of L-lactide is low. Thus, lactide of high purity isolated by the method can be usefully used for the production of polylactide having high molecular weight.

EXAMPLES

Figure 1:
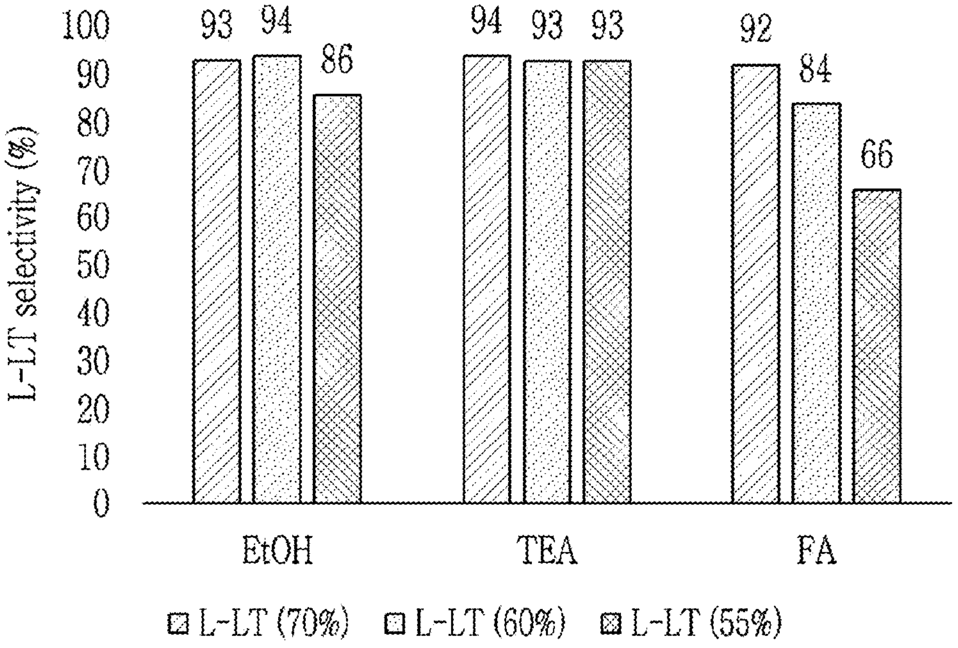
FIG. 1 is a graph showing the results of evaluating L-LT extraction selectivity according to introduced seed and L-LT rate.

Hereinafter, embodiments of the invention will be explained in more detail in the following examples. However, these examples are presented only as the illustrations of the invention, and scope of the invention is not limited thereby.

Example 1

Into 0.25 g of Rac-LT (weight ratio of L-LT: D-LT=1:1), 0.16 g of L-LT (introduction amount of L-LT, based on 100 parts by weight of Rac-LT=64 parts by weight) was introduced and mixed, thus preparing a mixture wherein the weight ratio of L-LT: D-LTis 7:3 (L-LT content based on the total weight of the mixture=70 wt %).

Into the mixture, 1.30 ml of triethylamine (TEA, melting point: −114.70° C., boiling point: 89.3° C.) (corresponding to 3.28 parts by weight, based on 1 part by weight of L-lactide existing in the mixture) was introduced, and stirred at room temperature for 1 hour. The resulting solution was in the state of an emulsion, and the solid parts were separated and removed by filtering through a filter, thus obtaining a filtrate.

Example 2

The same procedure as Example 1 was conducted, except that 0.07 g of L-LT (introduction amount of L-LT, based on 100 parts by weight of Rac-LT=28 parts by weight) was introduced into 0.25 g of Rac-LT (weight ratio of L-LT: D-LT=1:1), and mixed such that the weight ratio of L-LT: D-LT became 6:4 (L-LT content based on the total weight of the mixture=60 wt %).

Example 3

The same procedure as Example 1 was conducted, except that 0.03 g of L-LT (introduction amount of L-LT, based on 100 parts by weight of Rac-LT=12 parts by weight) was introduced into 0.25 g of Rac-LT (weight ratio of L-LT: D-LT=1:1), and mixed such that the weight ratio of L-LT: D-LT became 5.5:4.5 (L-LT content based on the total weight of the mixture=55 wt %).

Example 4

The same procedure as Example 1 was conducted, except that 0.84 ml of formamide (FA, melting point: 2° C., boiling point: 210° C.) (corresponding to 3.31 parts by weight, based on 1 part by weight of L-lactide existing in the mixture) was introduced instead of 1.30 ml of triethylamine.

Example 5

The same procedure as Example 2 was conducted, except that 0.84 ml of formamide (corresponding to 4.95 parts by weight, based on 1 part by weight of L-lactide existing in the mixture) was introduced instead of 1.30 ml of triethylamine.

Example 6

The same procedure as Example 3 was conducted, except that 0.84 ml of formamide (corresponding to 6.18 parts by weight, based on 1 part by weight of L-lactide existing in the mixture) was introduced instead of 1.30 ml of triethylamine.

Example 7

The same procedure as Example 1 was conducted, except that 1.17 ml of tri-n-octylamine (melting point: −34.0° C., boiling point: 367° C.) (corresponding to 3.31 parts by weight, based on 1 part by weight of L-lactide existing in the mixture) was introduced instead of 1.30 ml of triethylamine.

Example 8

The same procedure as Example 2 was conducted, except that 1.17 ml of tri-n-octylamine (corresponding to 4.87 parts by weight, based on 1 part by weight of L-lactide existing in the mixture) was introduced instead of 1.30 ml of triethylamine.

Example 9

The same procedure as Example 1 was conducted, except that 1.17 ml of tri-n-octylamine (corresponding to 6.12 parts by weight, based on 1 part by weight of L-lactide existing in the mixture) was introduced instead of 1.30 ml of triethylamine.

Comparative Example 1

The same procedure as Example 1 was conducted, except that 1.204 ml of ethanol (EtOH, melting point: −114.1° C., boiling point: 78.4° C.) was introduced instead of 1.30 ml of triethylamine.

Comparative Example 2

The same procedure as Example 2 was conducted, except that 1.204 ml of ethanol was introduced instead of 1.30 ml of triethylamine.

Comparative Example 3

The same procedure as Example 3 was conducted, except that 1.204 ml of ethanol was introduced instead of 1.30 ml of triethylamine.

Comparative Example 4

The same procedure as Example 1 was conducted, except that 0.92 ml of 1,4-dioxane (melting point: 11° C., boiling point: 101° C.) was introduced instead of 1.30 ml of triethylamine.

Comparative Example 5

The same procedure as Example 2 was conducted, except that 0.92 ml of 1,4-dioxane was introduced instead of 1.30 ml of triethylamine.

Comparative Example 6

The same procedure as Example 3 was conducted, except that 0.92 ml of 1,4-dioxane was introduced instead of 1.30 ml of triethylamine.

Comparative Example 7

The same procedure as Example 1 was conducted, except that L-LT was not introduced into Rac-LT as a seed.

Specifically, into Rac-LT (weight ratio of L-LT: D-LT=1:1), 1.30 ml of triethylamine (corresponding to 7.6 parts by weight, based on 1 part by weight of L-lactide existing in the mixture) was introduced, and stirred at room temperature for 1 hour.

However, in the resulting solution, separation of solid corresponding to D-LT did not occur.

Experimental Example (1) L-LT Extraction Selectivity

For each filtrate obtained in Examples and Comparative Examples, the weight ratio of L-LT: D-LT was measured, and from the results, L-LT extraction selectivity was evaluated.

Specifically, about 60 μl of each filtrate obtained in Example and Comparative Example was taken and diluted in 1 ml of acetonitrile (MeCN) to prepare a sample for gas chromatography (GC) analysis. For the prepared sample, GC analysis was conducted under the following conditions. In the chromatogram obtained as the result of GC analysis, the total peak area and L-LT peak area were respectively calculated, and L-LT extraction selectivity (%) was calculated according to the following Mathematical Formula 1.

L-LT extraction selectivity (%)=(L−LT peak area/total peak area)×100 [Mathematical Formula 1]

In the Mathematical Formula 1, the total peak area and L-LT peak area were respectively calculated through integral of each peak.

<GC Analysis Conditions>

GC/FID, Shimadzu
Column: CP-Chirasil
Dilution solvent: MeCN (acetonitrile)
Injection volume: 1 μl
Injection port temperature: 200° C.
Carrier gas: $N_2$
FID (flame photometric detector) Temperature: 275° C.
Column temperature:
Carrier flow rate (ml/min): 1.5 ml/min
Analysis time: 19.60 min The results were shown in the following Table 1, and FIGS. 1 to 4.

Figure 2:
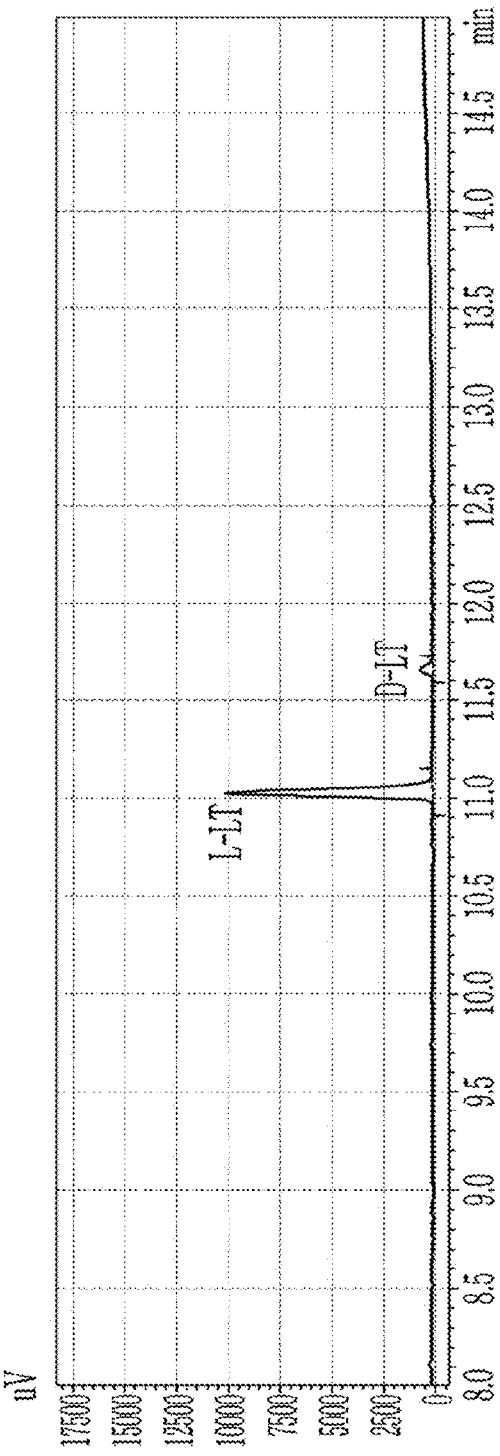
FIG. 2 is a graph showing the results of gas chromatography analysis of Example 3.
Figure 3:
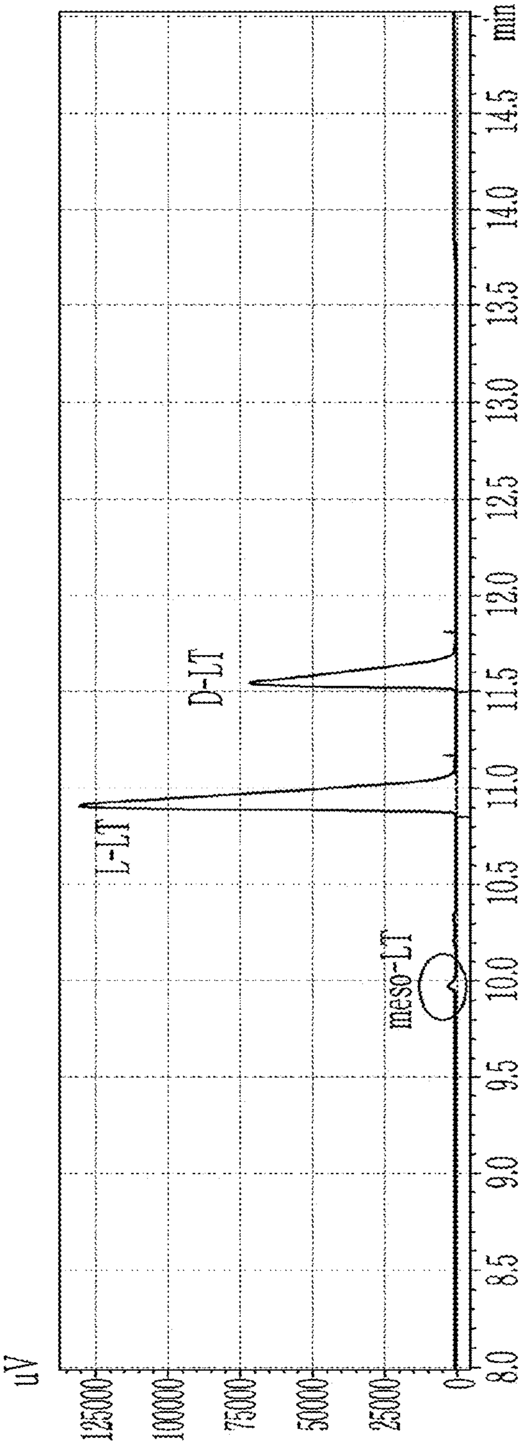
FIG. 3 is a graph showing the result of gas chromatography analysis of Example 6.
Figure 4:
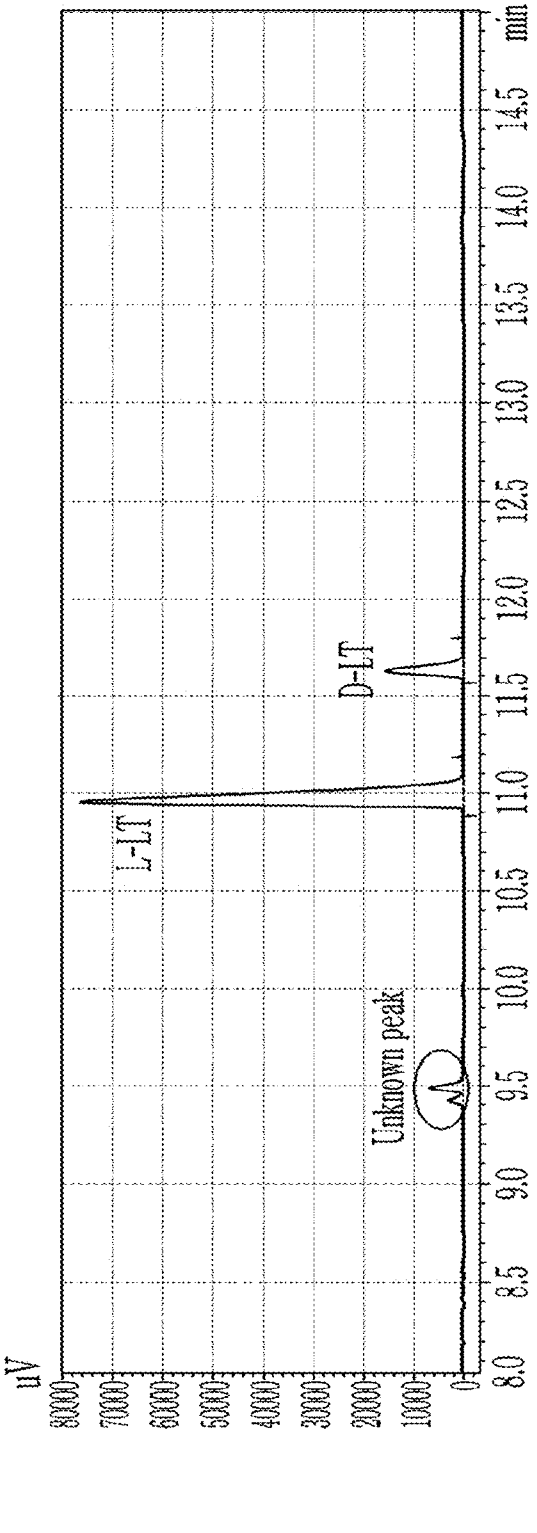
FIG. 4 is a graph showing the result of gas chromatography analysis of Comparative Example 3.

FIG. 1 is a graph showing the results of evaluating L-LT extraction selectivity according to introduced seed and L-LT rate, and FIGS. 2 to 4 are graphs respectively showing the gas chromatography analysis results of Example 3, Example 6 and Comparative Example 3.

In the gas chromatography analysis graphs of FIGS. 2 to 4, although x axis starts at O min where the analysis began, it is enlarged from 8 min where peaks began to be observed so as to clearly identify the results.

(2) Impurity Content (%)

From the GC analysis results, the contents of impurities generated during the isolation of racemate lactides according to Examples and Comparative Examples were measured.

Specifically, in the GC analysis chromatogram, the areas of peaks corresponding to impurities such as meso-LT peak and unknown peaks (hereinafter, simply referred to as 'impurity peaks') were respectively calculated, and impurity content (%) was calculated according to the following Mathematical Formula 2.

Impurity content (%)=(total area of impurity peaks/total peak area)×100 [Mathematical Formula 2]

In the Mathematical Formula 2, the total peak area and the area of impurity peak are respectively calculated through integral of each peak, and the total area of impurity peaks means the sum of impurity peak areas calculated through integral.

TABLE 1

| | Weight ratio of L-LT:D-LT in the mixture, after introducing L-LT | Extraction solvent | Weight ratio of L-LT:D-LT in the finally obtained filtrate | L-LT extraction selectivity (%) | Impurity content (%) |
|---|---|---|---|---|---|
| Example 1 | 70:30 | TEA | 94.5:5.5 | 94.491 | 0 |
| Example 2 | 60:40 | TEA | 93.5:6.5 | 93.538 | 0 |

TABLE 1-continued

| | Weight ratio of L-LT:D-LT in the mixture, after introducing L-LT | Extraction solvent | Weight ratio of L-LT:D-LT in the finally obtained filtrate | L-LT extraction selectivity (%) | Impurity content (%) |
|---|---|---|---|---|---|
| Example 3 | 55:45 | TEA | 93.9:6.1 | 93.926 | 0 |
| Example 4 | 70:30 | FA | 92.0:8.0 | 92.045 | 0.643 |
| Example 5 | 60:40 | FA | 84.0:16.0 | 84 | 0.884 |
| Example 6 | 55:45 | FA | 66.1:33.9 | 66.069 | 0.928 |
| Example 7 | 70:30 | Tri-n-octylamine | 93.5:6.5 | 93.529 | 0 |
| Example 8 | 60:40 | Tri-n-octylamine | 92.9:7.1 | 92.929 | 0 |
| Example 9 | 55:45 | Tri-n-octylamine | 93.2:6.8 | 92.884 | 0 |
| Comparative Example 1 | 70:30 | EtOH | 94.0:6.0 | 93.963 | 11.782 |
| Comparative Example 2 | 60:40 | EtOH | 94.3:5.7 | 94.266 | 6.940 |
| Comparative Example 3 | 55:45 | EtOH | 86.5:13.5 | 86.547 | 5.227 |
| Comparative Example 4 | 70:30 | 1,4-dioxane | 79.2:20.8 | 79.252 | 0 |
| Comparative Example 5 | 60:40 | 1,4-dioxane | 66.3:33.7 | 66.274 | 0 |
| Comparative Example 6 | 55:45 | 1,4-dioxane | 57.9:42.1 | 57.898 | 0 |

As the results of experiment, Examples 1-9 wherein TEA, FA or Tri-n-octylamine was used as an extraction solvent exhibited excellent L-LT extraction selectivities and remarkably decreased impurity contents.

Specifically, in case a L-LT rate in the mixture after introducing L-LT was 60 wt % or more, Examples, 1, 2, 4, 5, 7 and 8 wherein TEA, FA or Tri-n-octylamine was used as an extraction solvent exhibited L-LT extraction selectivities equivalent to or more excellent than those of Comparative Examples 1, 2, 4 and 5.

And, in case a L-LT rate in the mixture after introducing L-LT was less than 60%, specifically as low as 55%, the conventional extraction solvent EtOH exhibited decreased L-LT extraction selectivity of 86.547%, while TEA and Tri-n-octylamine still exhibited high L-LT extraction selectivities of 92.045% and 92.884%, respectively.

Meanwhile, in the case of Example 6 wherein FA was used as an extraction solvent, L-LT extraction selectivity was 66.069%, which was lower than that of Comparative Example 3 using EtOH. However, the content of impurities generated during the isolation of lactide racemate using FA was 0.928%, while the content of impurities generated during the isolation of lactide racemate using EtOH was 5.227%, which was remarkably high. Thus, it can be seen that in case an L-LT content is low, when FA is used as an extraction solvent, L-LT extraction selectivity is rather lower compared to the case of using EtOH, but since impurity content can be remarkably decreased, L-LT can be obtained with higher purity.

And, as shown in the GC analysis graphs of FIGS. 2 to 4, in the case of Example 3 using TEA, peaks other than L-LT and D-LT did not exist in the GC analysis graph. To the contrary, in the case of Comparative Example 3 using an EtOH solvent, unknown peaks other than L-LT and D-LT were observed in the GC analysis graph, confirming the possibility of side reactions of lactide such as hydrolysis, and the like.

And, in the case of Example 6 using FA, very small meso-LT peak was observed in the section of retention time-10 minutes or more in the GC analysis graph, thus confirming the existence of side reactions. However, since the rate is very low, the content of by-products was also very small.

The invention claimed is:

1. A method for isolating lactide racemate, comprising:

introducing L-lactide into lactide racemate and mixing them to prepare a mixture; and introducing an extraction solvent into the mixture, to selectively extract L-lactide from the lactide racemate, wherein the extraction solvent comprises an amine-based compound or an amide-based compound.

2. The method according to claim 1, wherein the extraction solvent is liquid, and has a melting point of 25° C. or less and a boiling point of 80° C. or more.

3. The method according to claim 1, wherein the extraction solvent is a non-chiral compound.

4. The method according to claim 1, wherein the amine-based compound is a tertiary amine of Chemical Formula 1:

[Chemical Formula 1]

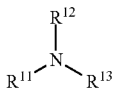

wherein:

$R_{11}$ to $R_{13}$ are each independently a $C_{1-20}$ linear or branched alkyl.

5. The method according to claim 1, wherein the amine-based compound is trimethylamine, triethylamine, tri-n-propylamine, tri-n-butylamine, tri-n-octylamine, tridodecylamine, trioctadecylamine, triisopropylamine, triisobutylamine, tri-t-butylamine, tris(2-ethylhexyl) amine, N,N-dimethyloctylamine, N,N-dimethyldodecylamine, N,N-dimethyl-n-octadecylamine, or N,N-diethyldodecylamine.

6. The method according to claim 1, wherein the amine-based compound is triethylamine, or tri-n-octylamine.

7. The method according to claim 1, wherein the amide-based compound is formamide, or dimethylacetamide.

8. The method according to claim 1, wherein the extraction solvent is used in an amount of 1 to 10 parts by weight, based on 1 part by weight of L-lactide existing in the mixture.

9. The method according to claim 1, wherein the L-lactide is introduced in an amount of 10 to 70 parts by weight, based on 100 parts by weight of the lactide racemate.

10. The method according to claim 1, wherein the L-lactide is introduced in such an amount that the content of L-lactide in the mixture becomes greater than 50 wt % and 80 wt % or less, based on the total weight of the mixture.

11. The method according to claim 1, wherein the L-lactide is introduced in such an amount that the content of L-lactide in the mixture becomes greater than 50 wt % and less than 60 wt %, based on the total weight of the mixture.

* * * * *